(12) United States Patent
Liu et al.

(10) Patent No.: US 12,415,066 B2
(45) Date of Patent: Sep. 16, 2025

(54) BIOMIMETIC STIMULATOR SYSTEM FOR NEURAL IMPLANT

(71) Applicant: THE REGENTS OF THE UNIVERSITY OF CALIFORNIA, Oakland, CA (US)

(72) Inventors: Wentai Liu, Los Angeles, CA (US); Stanislav Culaclii, Los Angeles, CA (US); Po-Min Wang, Los Angeles, CA (US); Yi-Kai Lo, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 460 days.

(21) Appl. No.: 17/813,377

(22) Filed: Jul. 19, 2022

(65) Prior Publication Data

US 2022/0409886 A1 Dec. 29, 2022

Related U.S. Application Data

(63) Continuation of application No. PCT/US2021/014829, filed on Jan. 24, 2021.
(Continued)

(51) Int. Cl.
*A61N 1/36* (2006.01)
*A61N 1/05* (2006.01)
(Continued)

(52) U.S. Cl.
CPC ....... *A61N 1/0551* (2013.01); *A61N 1/36153* (2013.01); *A61N 1/36175* (2013.01);
(Continued)

(58) Field of Classification Search
CPC ................. A61N 1/36146; A61N 1/36175
See application file for complete search history.

(56) References Cited

U.S. PATENT DOCUMENTS

| 5,370,672 A | 12/1994 | Fowler |
| 10,702,696 B2 * | 7/2020 | Grill ................. A61N 1/36062 |

(Continued)

FOREIGN PATENT DOCUMENTS

| WO | 2017210491 A1 | 12/2017 |
| WO | 2021151050 | 7/2021 |

OTHER PUBLICATIONS

ISA/US, United States Patent and Trademark Office (USPTO), International Search Report and Written Opinion issued Apr. 21, 2021, related PCT international application No. PCT/US2021/014829, pp. 1-29, with claims searched, pp. 30-38.

*Primary Examiner* — Eric D. Bertram
(74) *Attorney, Agent, or Firm* — O'BANION & RITCHEY LLP; John P. O'Banion

(57) ABSTRACT

A neural stimulator system which generates stimulation from an implantable stimulator circuit which generates stimulation outputs which mimic biological signals. The user/operator can select stimulation generated from recorded waveforms, or by selecting the characteristics for generating stimulation based on randomized inter-pulse-intervals (IPI). A control unit controls the operation of the implantable stimulator circuit, and receives sets of stimulation parameters based on user input from a user input device executing application specific programming.

22 Claims, 9 Drawing Sheets

Related U.S. Application Data

(60) Provisional application No. 62/965,875, filed on Jan. 25, 2020.

(51) Int. Cl.
*A61N 1/372* (2006.01)
*A61N 1/378* (2006.01)

(52) U.S. Cl.
CPC ..... *A61N 1/37223* (2013.01); *A61N 1/37247* (2013.01); *A61N 1/3727* (2013.01); *A61N 1/3787* (2013.01)

(56) References Cited

U.S. PATENT DOCUMENTS

| | | | |
|---|---|---|---|
| 11,103,708 B2* | 8/2021 | Grill | A61N 1/36146 |
| 2003/0144710 A1* | 7/2003 | Haugland | A61F 2/72 |
| | | | 607/48 |
| 2012/0259383 A1* | 10/2012 | Trier | A61N 1/3625 |
| | | | 607/46 |
| 2015/0080987 A1* | 3/2015 | Decre | A61N 1/36025 |
| | | | 607/62 |
| 2015/0127066 A1* | 5/2015 | Grill, Jr. | A61N 1/36082 |
| | | | 607/59 |
| 2017/0043166 A1* | 2/2017 | Choi | A61B 5/4064 |
| 2018/0064943 A1* | 3/2018 | Grill | A61N 1/37247 |
| 2020/0316384 A1* | 10/2020 | Grill | G16H 20/40 |

\* cited by examiner

BIOMIMETIC STIMULATOR SYSTEM FOR NEURAL IMPLANT

CROSS-REFERENCE TO RELATED APPLICATIONS

This application claims priority to, and is a 35 U.S.C. § 111(a) continuation of, PCT international application number PCT/US2021/014829 filed on Jan. 24, 2021, incorporated herein by reference in its entirety, which claims priority to, and the benefit of, U.S. provisional patent application Ser. No. 62/965,875 filed on Jan. 25, 2020, incorporated herein by reference in its entirety. Priority is claimed to each of the foregoing applications.

The above-referenced PCT international application was published as PCT International Publication No. WO 2021/151050 A1 on Jul. 29, 2021, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to neural stimulation devices, and more particularly to a neural interface implant that provides stimulation waveforms that mimic standard biological signals.

2. Background Discussion

Electrical neural stimulation is an effective method of modulating the nervous systems for the purposes of therapeutics and research of neurologic diseases. Typical neural stimulation involves delivery of periodic electrical current to the tissue at predefined times and spans. This has been shown to be useful in deep brain stimulation (DBS) therapy for treating motor disorders due to Parkinson's disease, rehabilitation after spinal cord injury to restore motor functions, epiretinal prosthesis to enable vision for the blind, and in other areas.

Recently it has also been demonstrated that non-periodic, non-uniform stimulation is more effective in these applications. For example, a stimulus pattern mimicking a pre-recorded electromyography (EMG) signal is more effective in activating spinal cord locomotion circuits compared to uniformly periodic protocol. In addition, neuromodulation using non-regularly timed stimuli for DBS has produced improved therapeutic effects for treating Parkinson's disease. Finally, stimuli timed with a random exponential distribution prevent adaptation of retinal ganglion cells, promising to reduce undesired image "fading" effect in an epiretinal prosthesis.

However, biomimetic stimulation patterns of this type require a sophisticated stimulator solution. The most common approaches use bulky stimulators which can mimic a preloaded waveform, e.g. computer with a data acquisition (DAQ) device or desktop stimulator. These commercial devices are not translatable to either implantable applications or a responsive system which can adjust its stimulation based on the bio-recordings in real-time. A few implantable and programmable neural stimulators, which have been demonstrated, adjust their pulse widths and firing frequencies, or turn on or off based on external commands; yet they fail to mimic biological waveforms.

Accordingly, a need exists for biomimetic electrical stimulation which provides enhanced effectiveness in treatment and therapy regimes, while being practical for implantable devices. The present disclosure fulfills that need and provides additional benefits over previous technologies.

BRIEF SUMMARY

This disclosure describes a neural interface implant that provides stimulation waveforms that mimic standard biological signals. The disclosed apparatus, system, and/or method is configured for adapting the value of each stimulation parameter in real-time to properly mimic biological signal waveforms.

An implantable multiple channel neural stimulator system is described. By way of example, and not of limitation, the present disclosure exemplifies this design using a neural stimulator system having multiple channels based on an implantable System-On-Chip (SoC).

The system is designed to be portable, wirelessly controlled, and sufficiently versatile to perform concurrent multi-channel stimulation with independent arbitrary waveforms. Experimental results demonstrate multi-channel stimulation mimicking electromyography (EMG) waveforms, similar neural waveform representations, and randomly-spaced stimulation pulses mimicking neural firing patterns. This compact and flexible system is configured to support various forms of neuromodulation research as well as animal studies and serves as a precursor for the development of the next generation implantable biomimetic stimulator.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

1. Introduction

The disclosed biomimetic stimulator provides numerous benefits for research and treatment, and may be implemented in numerous ways. By way of example, the following discussion describes an implementation (embodiment) of a biomimetic stimulator platform that is based on a wireless stimulator circuit which can form the basis of an implantable system capable of biomimetic stimulation for various applications, and at least one embodiment of which can provide real-time closed-loop, bidirectional control of biomimetic stimulation.

Figure 1:
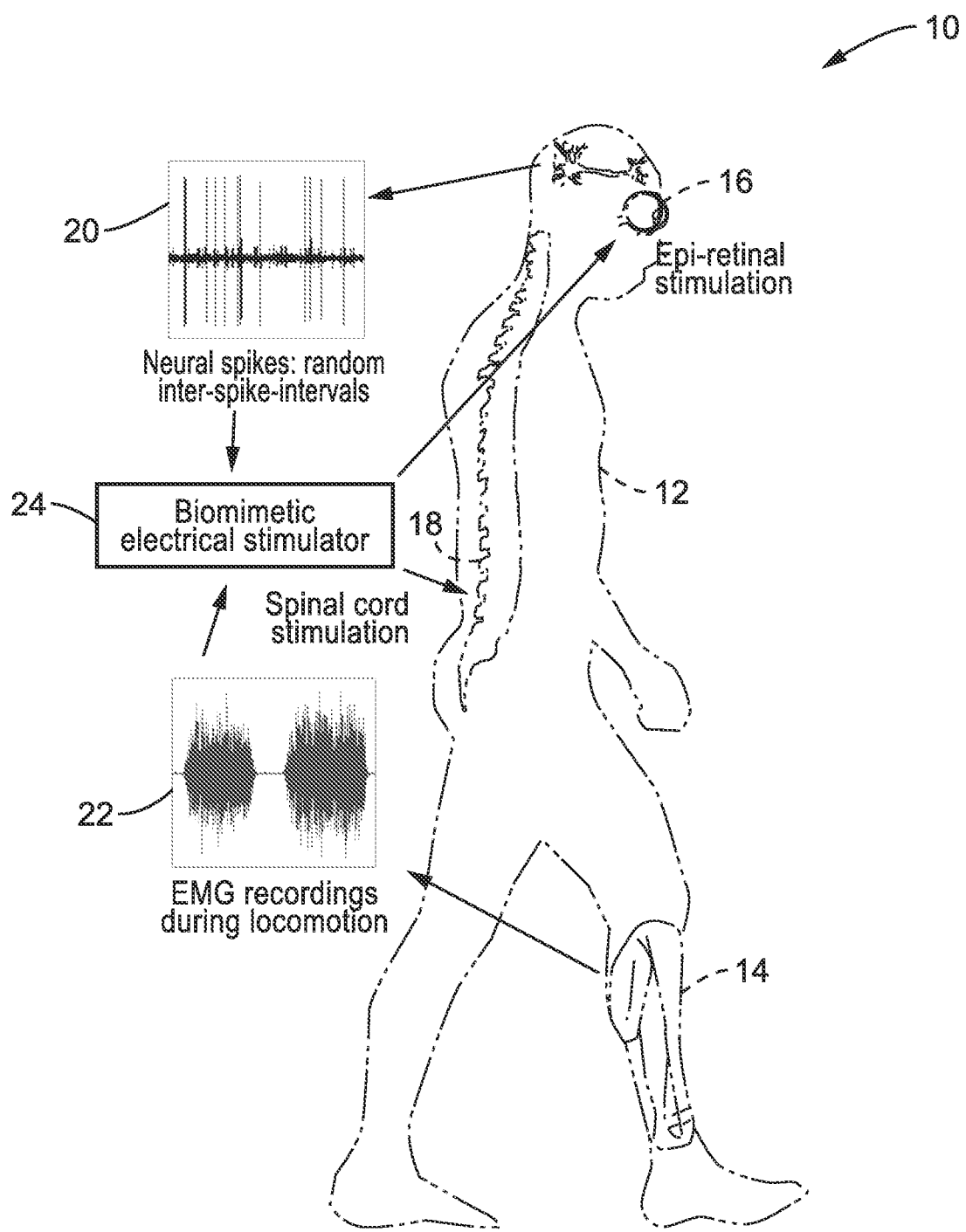
FIG. 1 is a block diagram showing a general application of the disclosed next-generation biomimetic stimulator according to at least one embodiment of the present disclosure.

FIG. 1 illustrates an example embodiment 10 of a biomimetic stimulator system. This prototype provides a reliable, battery-powered platform for evaluation of biomimetic stimulation therapy. The system also provides a means for enhancing existing wireless implant systems for use with a biomimetic stimulation mode.

In the figure is seen a general context depicting applications of a next-generation biomimetic stimulator according to an embodiment of the presented technology. A subject is shown as an example, from which an example EMG recording 22 was recorded during locomotion, as received by, or communicated to, the biomimetic stimulator system 24. The system 24 generates biomimetic stimulation to areas of the subject, exemplified here but not limited to, spinal cord stimulation 18 and central nervous system stimulation 16, and obtains information 20 on neural response for optimizing operation. The stimulation waveform can also be derived through recorded neural signals, such as local field potential and action potentials from central, peripheral, and autonomic nervous systems, and/or other physiological signals including but not limited to electrocardiogram (ECG).

2. Design of the Biomimetic Waveform Stimulator

2.1 System Architecture

Figure 2A:
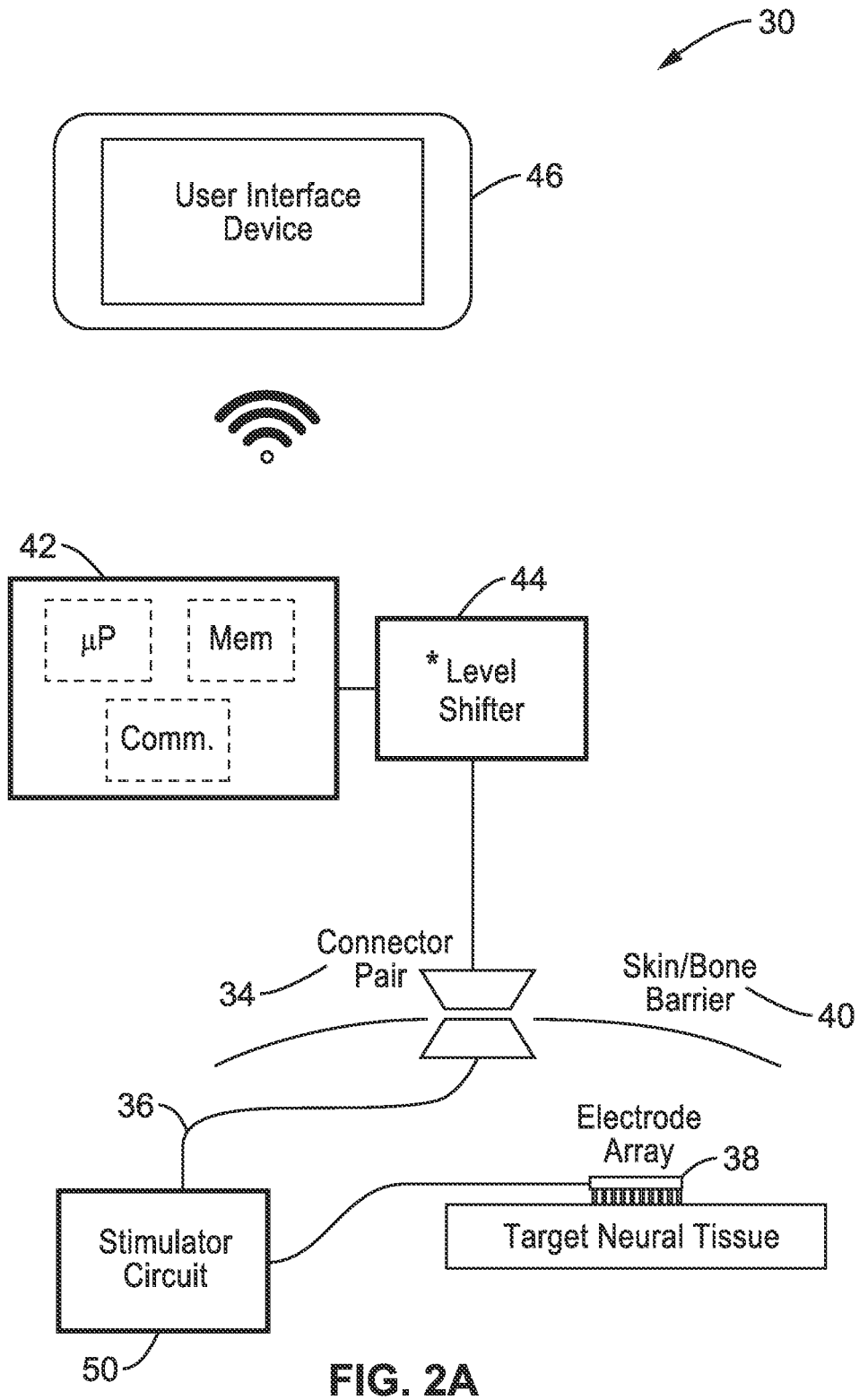
FIG. 2A and FIG. 2B are block diagrams of a biomimetic stimulator system according to embodiments of the present disclosure.
Figure 2B:
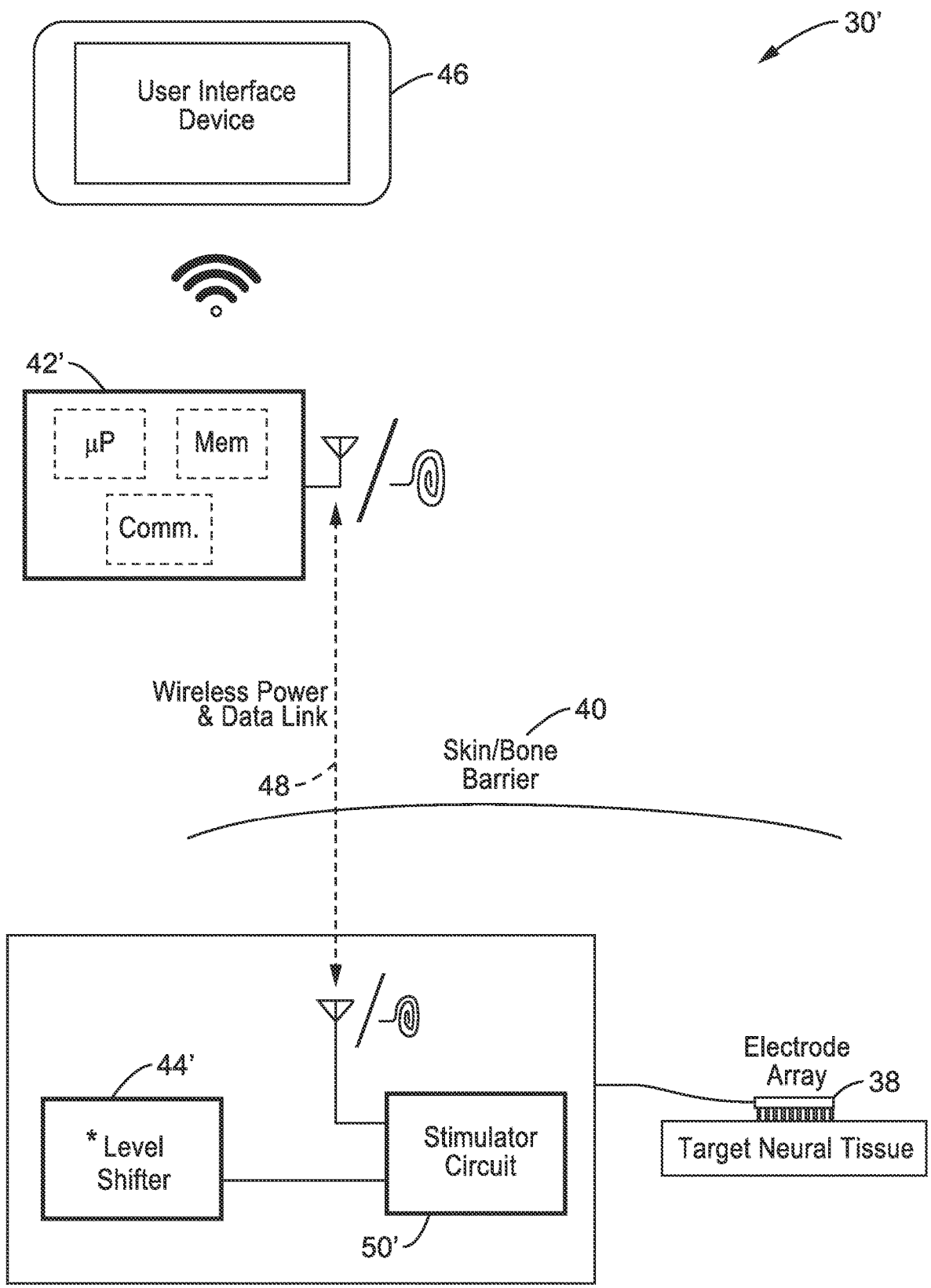

FIG. 2A and FIG. 2B illustrate example embodiments 30, 30' of biomimetic-waveform stimulators designed to support features of portability, wireless user interface, user-defined arbitrary stimulation patterns and concurrent multi-channel stimulation. Stimulation is controlled across one or multiple channels, with at least one embodiment describing 32-channels, although this may be expanded to hundreds of channels as desired. The outputs of the stimulator circuit are coupled to an electrode array which interacts with biological tissues.

The first embodiment 30 in FIG. 2A of the biomimetic stimulator is configured with a wired connection to the neural implant, while the second embodiment 30' in FIG. 2B illustrates a wireless connection to the neural implant.

Referring to FIG. 2A a control unit 42 comprises a processor (e.g., microcontroller) and its associated memory, a communication circuit, as well as power and data circuits. The processor of control unit 42 generates data packets for current/voltage waveform specifications at every channel. Output from the control unit are directed through an optional level shifter 44 before being connected, via a wired connector 34 and wiring 36, to a stimulator circuit 50 for controlling amplitude of the output signals when these data packets are translated into real current/voltage waveforms and delivered through driver circuitry to electrode array 38 for stimulating target neural tissue, such as below the skin/bone barrier 40.

The digital signals can be carried by one or more signal lines in the wiring from control unit 42, or optional level shifter 44, to stimulator circuit 50. It at least one embodiment the data packets for all channels are carried over a single signal wire, or a differential pair, although this can be split across any number of signal lines as desired. Each packet has a header, a tail and a payload of real data which comprises either configuration information or stimulation waveforms. Different headers provide differentiation between configuration data and stimulation data. In at least one preferred embodiment, error detection/error correction is performed on the packets. In at least one embodiment, upon receiving the packet, the operation of configuration or stimulation starts immediately. In at least one embodiment the stimulator circuit includes an internal clock which controls circuit operation once the stimulation operation commences. It should be appreciated that the packaging of the data as described above, is given by way of example and not limitation, and the digital data may be packaged in other ways without departing from the teachings of the present disclosure.

In at least one embodiment this stimulator circuit can be implemented as a System-On-Chip (SoC) wherein references to SoC thus refer to this stimulator circuit.

A user interface device 46 contains custom application programming for controlling control circuit 42 through a wireless communications interface, such as using WiFi and Bluetooth.

Referring now to FIG. 2B, it will be noted that in view of the wireless connection to the stimulator circuit 50', the optional level shifter circuit 44 from FIG. 2A is now moved into a modified version 44' and performs more along the lines of power conversion from the power sources used for driving the stimulator circuit. The modified stimulator circuit 50' now has a communication circuit which operates wirelessly. Control unit 42' is shown with a processor, memory and communications circuits which also provide wireless communications between control unit 42' and the stimulator circuit 50' and its optional level shifter 44'. This wireless communications can take numerous forms, including using RF communications as shown in the figure or inductive near field communications, in which inductive loops are shown as alternatives for the depicted antennas.

The power for driving stimulator circuit 50' may be supplied from stored power and/or received power, and may be processed by optional level shifter 44'. Stored power sources may be attached to the stimulator circuit, (e.g., battery or capacitive sources, fuel cells, blood plasma driven fuel cells, or other sources). Alternatively, or additionally, power may be coupled to the stimulator circuit, such as through an RF connection using a recent technology often referred to as power-over-distance wireless charging technology (e.g., from Powercast™), or the well established near field inductive power transfer wherein the antennas represented in FIG. 2B are replaced by one or more inductive coils as shown.

In at least one embodiment, the wireless connection to the implant comprises a near-field Wireless Power Transfer (WPT) mechanism utilizing an electromagnetic field for coupling power from the control unit to the implant, and for communicating data in either a single direction or bidirectionally between devices.

The control unit 42, 42' is configured for controlling the stimulator circuit 50, 50' and its electrode array in response to receiving user control inputs from a user interface 46 from which it receives user inputs, and to which it can in at least one embodiment generate outputs (e.g., visual, auditory, recorded data and/or haptic) for a user.

In at least one embodiment the level shifter 44, 44' is configured for shifting levels to an appropriate level for use in generating stimulation.

It should be appreciated that in at least one embodiment the communications interfacing to the stimulator circuit comprises a bidirectional communications link, such as a wired or wireless digital link. This link may take a number of forms, for example such as an I2C bus, wireless telemetry, near field inductive coupling, or other communications circuit configured for interfacing with the implant.

Although the present disclosure primarily describes the sending of data for controlling stimulation parameters the present disclosure is also configured for supporting simultaneous recording and stimulation, whereby the stimulation circuit also collects various operational and/or neurological information as stimulation feedback thus creating a real-time closed-loop, bidirectional, system. In this embodiment, the stimulation circuit is also configured for collecting stimulation feedback (FB) and transmitting it to the control unit. The control unit receives and processes the stimulation feedback and determines whether to directly update or modify the stimulation parameters being sent to the stimulation circuit, or to packetize the feedback for transmission to the user interface device, such as for display or recording.

In one embodiment, modification of the biomimetic stimulation waveforms includes, but is not limited to, waveform polarity, frequency, amplitude, and can be updated in response to receiving real-time recorded physiological signals (e.g., EMG, ECG, action potentials, and local field potential) by the closed-loop system. Thus, in at least one embodiment, the stimulator system is configured to provide closed-loop capabilities in which feedback collected from said stimulator circuit is utilized for updating and/or modifying said stimulation parameters. By way of example and not limitation consider the case of a spinal cord injury application, EMG responses can be recorded in real-time by the stimulator circuit and then relayed to the UI via bidirectional communications, while the EMG state-dependent feedback control algorithm at the UI responsively issues new stimulation commands, such as new stimulation protocols with a new frequency, amplitude, polarity, and/or phase at the stimulation electrodes. It should be appreciated that numerous forms of neural responses, physiological states, environmental conditions, or combinations thereof can be evaluated for determining if and what modification or alterations should be made to the stimulation protocols at a collective level or even down to the channel level.

In at least one embodiment, the stimulator circuit comprises a custom stimulator System-on-Chip (SoC) configured for connecting to an electrode array, or is packaged with the electrode array into the neural implant, or is configured for connecting to more than one electrode array.

The clock and commands required by the stimulator circuit for generating the stimulation outputs are sent from control unit 32 through a wired or wireless connection to the stimulator circuit. In at least one embodiment, the electrode array-stimulator circuit alternatively or additionally supports wireless power and data transmissions via telemetry coils, which allow the stimulation system to support implantable applications as needed.

The control unit is configured for coupling to a user interface (UI), such as by wireless communication, exemplified but not limited to, a WiFi link to a mobile device hosting application programming which has been specifically configured for controlling the disclosed biomimetic stimulator. This may be implemented using a dedicated mobile processing device, or installing applications programming described according the present disclosure, within an off-the shelf mobile processing device (e.g., a smart phone). The UI allows the ability for the user to remotely define stimulation patterns tailored for the described control unit and stimulation circuit for the targeted biomedical application.

The present disclosure describes a stimulator configured to perform multi-channel stimulation mimicking physiological signals EMG, ECG, action potential, local field potential waveforms and randomly-spaced stimulation pulses mimicking neuronal firing patterns; while achieving this in a manner which minimizes the size (volume) and power requirements of the implant.

It is worthy to note that this system design not only achieves a highly flexible and compact stimulation-platform technology but also in at least one embodiment incorporates the ability to support real-time closed-loop operations involving simultaneous recording and stimulation, by providing a data collection feedback circuit within the stimulator circuit as well as a communication path back to the control unit which is configured for receiving and in at least one embodiment storing (recording) this data and making it available through an external devices, such as a mobile user interface device (UI).

The user interface (UI) is also preferably configured with a high bandwidth (e.g., multi-channel) bidirectional communications protocol, such as the Wireless Fidelity (WiFi) standard. A WiFi type communications protocol may be preferred over one such as Bluetooth because WiFi provides a high data rate that can support more channels of wireless recording. In addition, use of a DC power source, such as a battery-power scheme, may be utilized to eliminate any potential 60 Hz noise toward increasing signal fidelity of recorded signals.

2.2 System Logic Design for Biomimetic Stimulation

The logic architecture of the system is designed to allow direct control of amplitude and width of each individual current/voltage pulse and their timing within the desired output waveform driven by the stimulator circuit. This control enables generating unique dynamic stimulation patterns, such as random pulse periods and biomimetic waveform generation on multiple stimulation output channels. The logic can be configured for compatibility with data protocols already utilized in existing stimulator devices.

Figure 3:
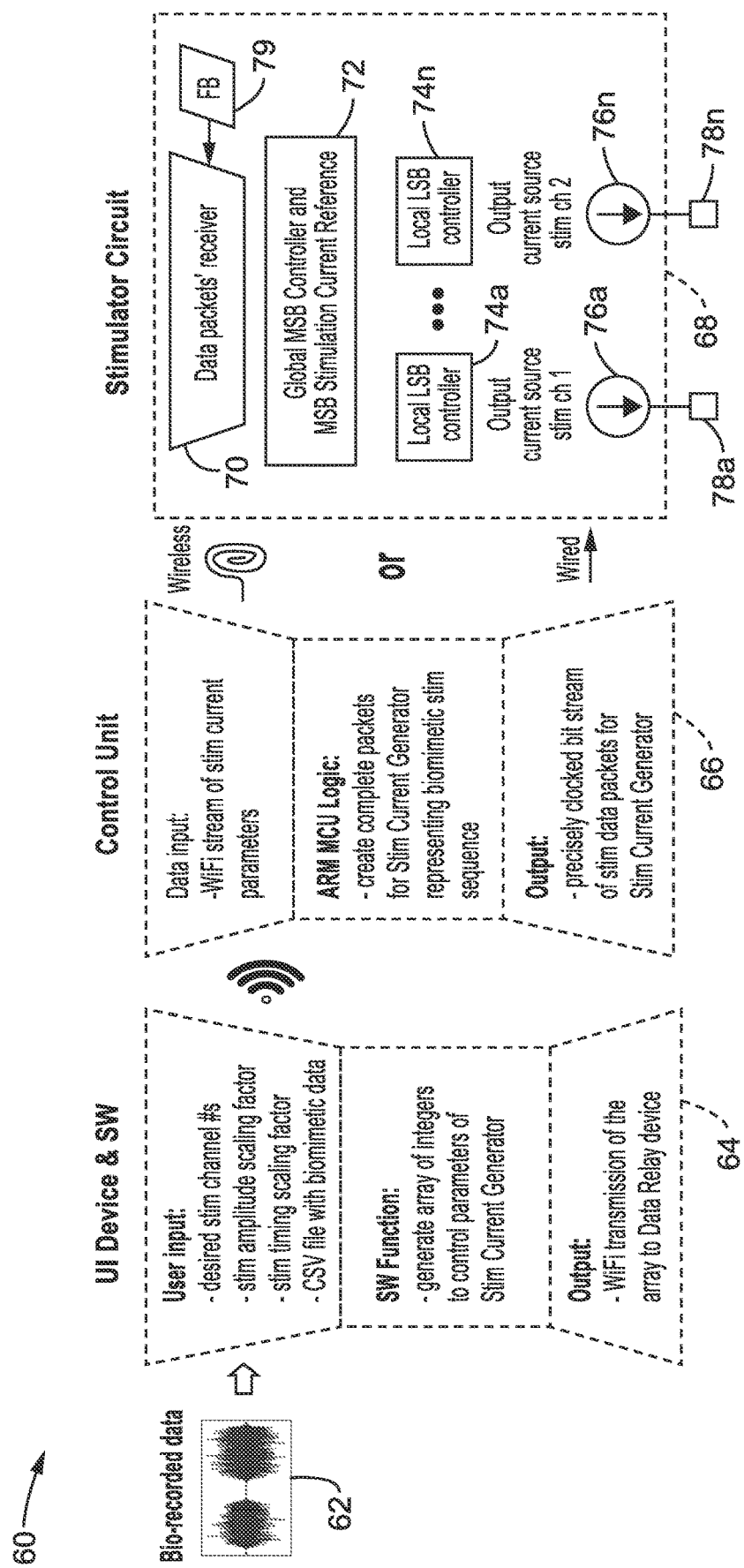
FIG. 3 is a logic flow diagram showing the sequence of control logic distributed between principle modules of the system according to at least one embodiment of the present disclosure.

FIG. 3 illustrates an example embodiment 60, with control logic distributed across three major components shown as a user-interface (UI) 64, data relay device and firmware in a control unit 66 and the implantable stimulator circuit 68.

User interface 64 comprises a mobile processor based electronics device for executing application programming (software) including an application programming for interacting with said control unit 66. In this example, the UI device is configured for receiving bio-recorded data 62 and processing this data to determine stimulation to be performed and generate associated commands, and stimulation parameters to be communicated to the control unit 66.

Application programming of the UI device is configured for obtaining user inputs on the desired stimulation channel numbers, stimulation amplitude scaling factor, stimulation time scaling factor, and selection of data, such as files containing biomimetic data or files with sets of predetermined settings or parameters or similar.

In response to these user settings the application programming generates commands and parameters, such as arrays of integers, to be sent to the control unit, for example over a wireless (e.g., WiFi) link.

The firmware executed by the microcontroller of control unit 66 receives these parameters and controls the stimulator circuit 68, such as by creating an object with stimulation command packets and sending them to the stimulator circuit. In response to receiving the commands and parameters from the UI device, the processor of the control unit creates complete data packets indicating stimulation current in a biomimetic stimulation sequence. These data packets are then precisely clocked into a bit stream of stimulation data packets sent (e.g., through a wired or wireless interface) to the stimulator circuit 68.

In at least one embodiment the stimulator circuit preferably comprises a very-large-scale integration (VLSI) circuit such as an SoC, which performs converting the incoming stream of stimulation data packets into actual stimulation signals to one or more stimulation electrodes, an array of stimulation electrodes, or to arrays of stimulation electrodes. The stimulator circuit is shown with a data packet receiver 70, a global MSB controller with MSB stimulation current reference 72, and multiple local LSB controllers 74a-74n which are coupled to output current sources 76a-76n which output stimulation current to each electrode 78a-78n. In addition stimulator circuit 68 is shown with an optional feedback circuit (FB) 79 for collecting stimulator feedback, for processing by the control unit and being transmitted back to the UI through blocks 66 and 64.

The logic architecture and data structures described are specifically configured to require higher computational demand at the UI level, then with reduced computational burden at the control unit level and with the least computational ability required of the implanted electrode array stimulator circuit. This design allows the implantable device to be implemented in a very compact form factor requiring minimal power consumption, toward reducing invasiveness for implantable applications. This logic architecture provides a unique data packet in real-time in response to the required stimulation parameters for each individual stimulus instance.

When using the system for stimulating with a biomimetic signal derived from physiological signal recording, the UI device is programmed by the user, such as within application programming, which receives user input to generate files or packetized transmissions describing the desired signal waveform. The biomimetic waveform is generated through either the pre-loading of physiological signals, or using real-time recorded physiological signals through the neural interface system, or a combination of both of these.

By way of example and not limitation, files can be generated with a format that is readable by the control circuit, for instance using digital files or digital streams, such as comma-space-variable (CSV) files, or packet streams, which may be sent to the control circuit which then collects and interprets the information for controlling the stimulator circuit.

In at least one embodiment, the waveform information is transferred as waveform profiles, such as represented by a set of integers (or other numerical representation) sent in a digital data stream (e.g., bit stream, packet stream, and/or file stream) to the control unit.

The control unit constructs full data packets from integers representing each data point, where the data packet defines the stimulation parameters in the format required by the stimulator circuit.

As seen in FIG. 3 this example format includes most significant bit (MSB) 72 and least significant bit (LSB) bit groups 74a-74n which define the stimulation pulse width and amplitude for each channel. The setting for the MSB is shared for all channels, while separate LSBs control each channel at every moment in time. Depending on the mode/configuration, both the MSB and LSB can or will be updated for the next stimulation time point and so forth.

The MSB controller 72 employs a current reference to define a gross scaling factor to the stimulation output for all channels thus controlling the total overall intensity of the stimulation. This MSB controller can also be updated in real-time with the next data packet, but all stimulation channels are affected by the MSB adjustment simultaneously.

The LSB controller(s) are a single controller configured to separately control each of a number of channels, or multiple LSB controllers which each handle a single channel or a group of channels. The LSB controller(s) employ a direct fine (more accurate) control of the current source by combining the MSB scaling factor with the exact local current output value to define the output current for that channel. This is also updated live (in real time) with each new data packet.

As the packet for each stimulus data point is created it is immediately sent to the stimulator circuit in real-time. The digital controller of the stimulator circuit configures internal registers with the bits from the data packet received and triggers (activates or fires) the stimulus current pulses in each channel accordingly. The process repeats at the pre-defined stimulation sample rate of the desired biomimetic stimulus waveform.

When the system is used to enable stimulation with randomized Inter-Pulse-Intervals (IPI), the user enters the average required stimulation IPI as user input into the UI device. The device generates an array of IPI following an exponential distribution with the required average following the equation:

$$T_n = \ln(U)/\lambda \qquad (1)$$

where $T_n$ is the pulse period for the n-th pulse, U is uniform probability distribution in a given range, and A, is the desired mean of IPI. An array containing the parameters of the stimulation current pulses and the randomized IPI values are then sent to the control unit. The remaining control logic flow is the same as that of the biomimetic stimulation.

3. Experimental Results

A biomimetic stimulator device prototype was produced in which the stimulator circuit was implemented in an SoC, which by way of example and not limitation, was packaged in a Quad-Flat-Pack (QFP) package to interface with the peripheral electronics. Bench top tests were conducted to demonstrate the versatility of waveforms generated by the stimulator, including randomized period pulse trains for use in retinal stimulation applications and EMG-mimetic stimulation patterns for spinal cord stimulation. In addition to spinal cord stimulation, this stimulator system can also be applied for neural stimulation of any part of the anatomy, and more typically to brain and peripheral nerve stimulations, where a non-uniform biomimetic stimulation protocol has shown to be advantageous over conventional repeating short pulse patterns. During testing, the stimulator was wirelessly controlled by custom application programming executing on an Android tablet, although other operating platforms can be utilized (e.g., IOS), which connects through a WiFi link to the control unit. Each stimulation output channel was simulated by being connected to a 10 kΩ resistive load.

Figure 4:
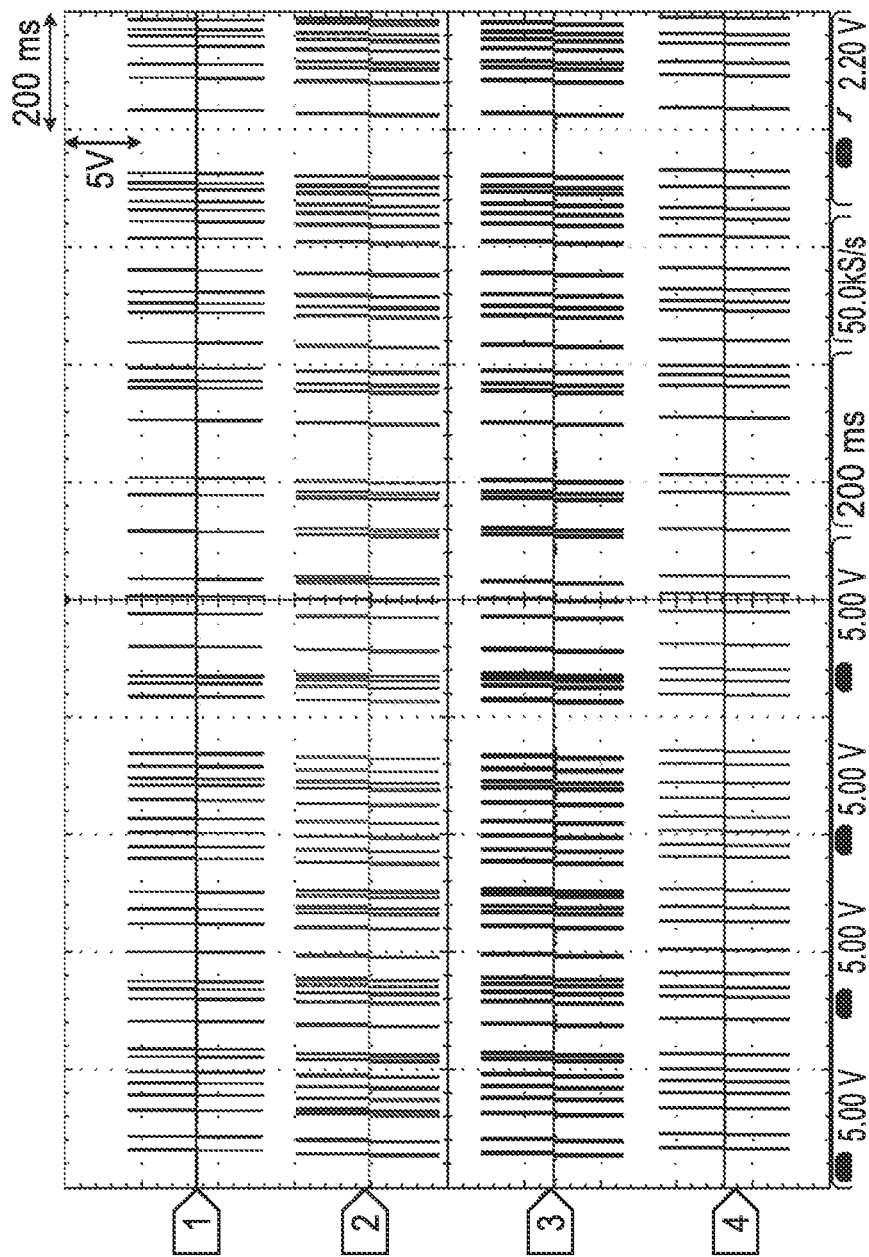
FIG. 4 and FIG. 5 are waveforms of measured multi-channel simulation with random IPI following exponential random distribution, with FIG. 5 providing a 10× magnified view along the time scale, as obtained according to at least one embodiment of the present disclosure.
Figure 5:
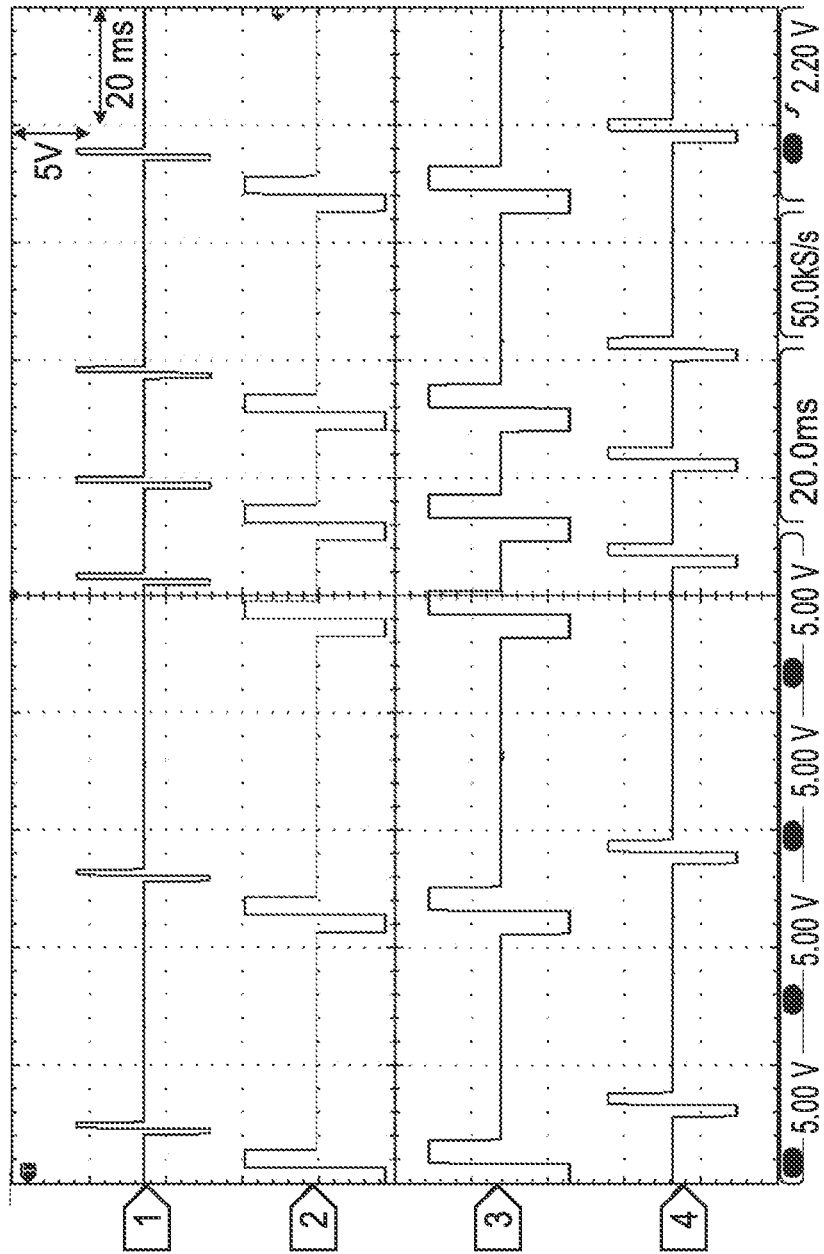

FIG. 4 and FIG. 5 illustrate an example of a randomized period pulse train 80 in FIG. 4 and in a 10× magnified view 90 on its time scale in FIG. 5 as generated by the prototype in the demonstration described above. It can be seen from the figure that the resulting multi-channel pulse trains exhibit random IPI which follows an exponential random distribution which have been shown to reduce undesired neural adaptation in epiretinal stimulation. The mean period of these stimulation outputs is 30 ms with current amplitudes set to 0.5 mA and pulse widths set between 1 and 4 ms among the available channels.

It should be appreciated, that although this specific application of the system only required one random IPI pattern without imposing a requirement for relative timing between multiple channels; the present disclosure is configured to provide randomness in relative timing (phase skews) between any number of channels as needed.

Figure 6:
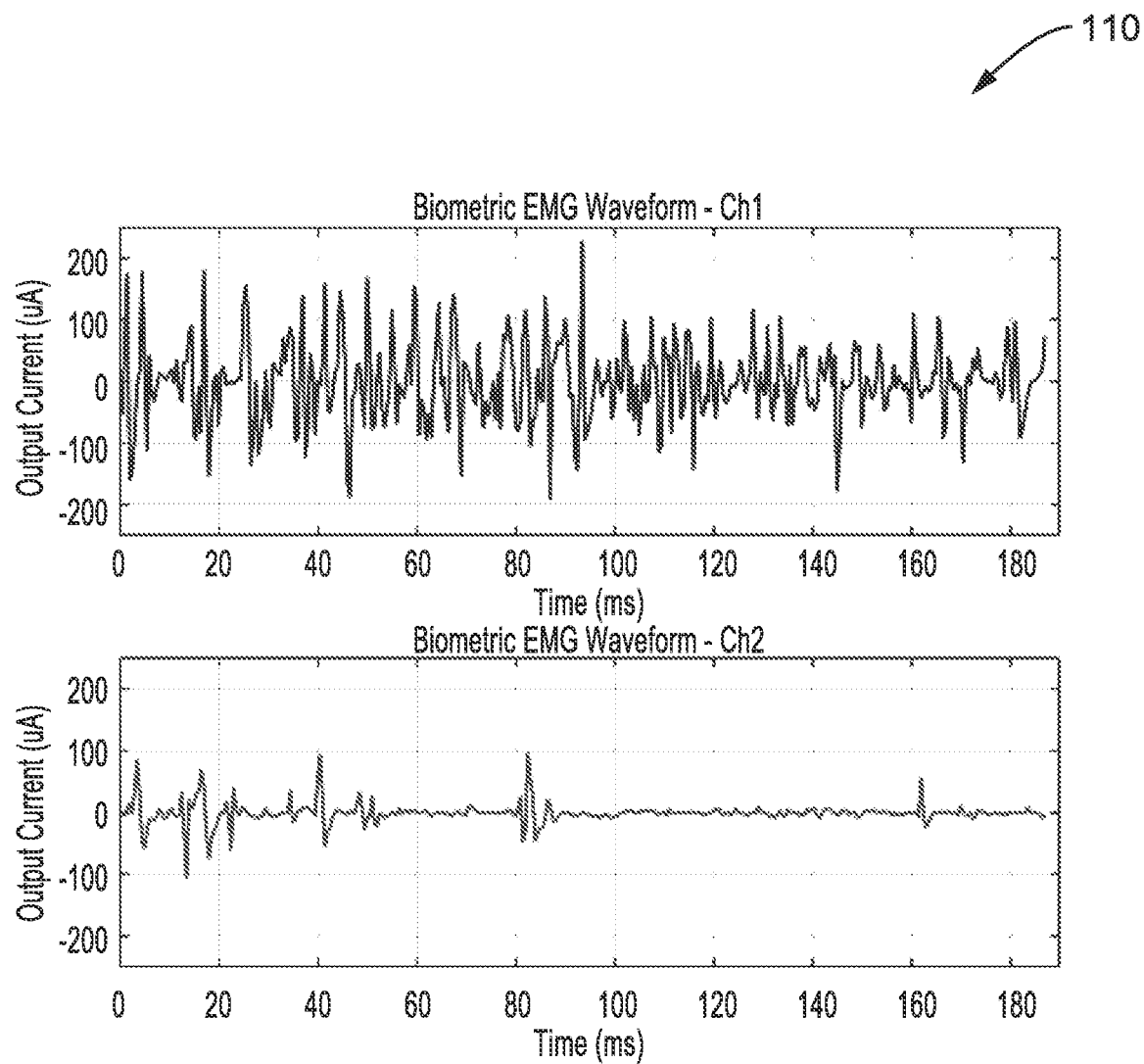
FIG. 6 and FIG. 7 are waveforms of multi-channel dynamic stimulation waveforms mimicking a recorded EMG waveform as generated by a demonstration of the disclosed stimulator, with FIG. 7 showing stimulation waveforms captured by an oscilloscope, according to at least one embodiment of the present disclosure.
Figure 7:
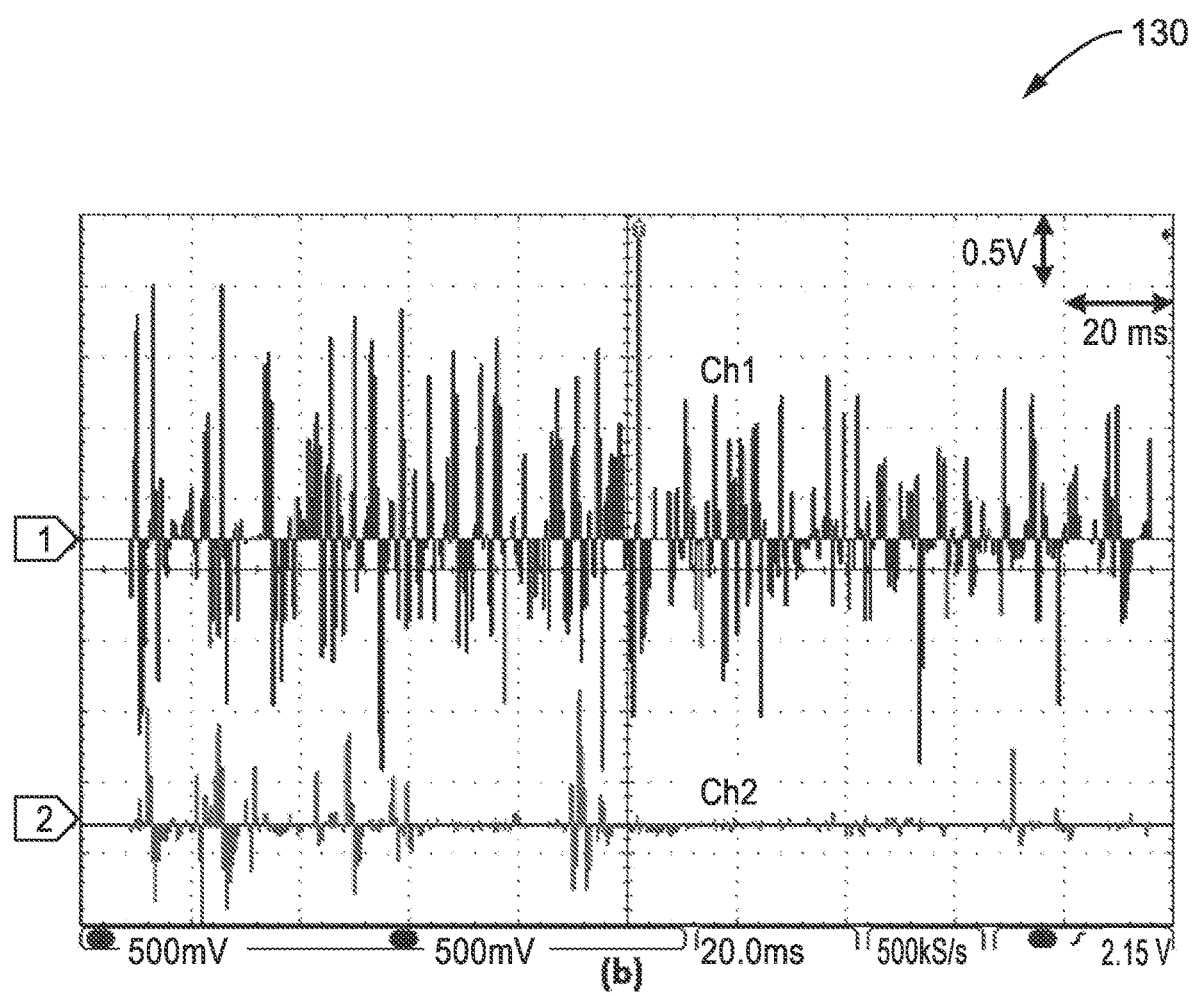

FIG. 6 and FIG. 7 illustrate example embodiments 110, 130, demonstrating the ability of the stimulator to generate biomimetic waveforms. In FIG. 6 is seen multiple channels (e.g., Ch1 and Ch2) of biometric EMG waveform signals having a desired stimulation waveform based on EMG recordings from the tibialis anterior (TA) of a rat during stepping. In FIG. 7 is seen the corresponding two channels of EMG-mimetic output generated by the stimulator as captured with an oscilloscope. In this present example the resolution of the output current amplitude supported by the stimulator circuit is 4 bits (digital-to-analog converter)+3 bits (variable-gain current mirror), although any desired number of bits can be utilized without departing from the teachings of the present disclosure. In the example shown, the temporal resolution of waveforms is 500 µs, measured from the start of one pulse to the next one, although other resolution levels may be adopted without departing from the present disclosure.

In the prototype (wireless transmission) it was found that within this 500 µs period there is a 100 µs gap with a null output, which appears between each two consecutive current samples in FIG. 7. In the prototype circuit, this gap appears to arise in response to wireless transmission of a command from the control unit to the digital controller of the stimulator circuit for processing, however the exact length of this gap will not affect the response of neural tissues as it much shorter than the refractory period of an individual neural cell which is approximately 1-2 ms.

One mechanism for eliminating this null gap, is to interleave multiple channels, so that as the controller of ch1 is outputting the stim current, ch2 is receiving the new command and will wait for a trigger to output it immediately after ch1 without a gap in timing. If ch1 and ch2 wires are connected together than a current will be output continuously from the joint wire (wire OR), eliminating the gap from a now single joint stimulation output.

Other solutions can be utilized, such as a simple shift register (e.g., parallel in serial output), which is loaded in parallel and sequenced as output with each output clock cycle, so that the processor can handle communications (or obtaining inputs) without interrupting output waveform generation. Other techniques, such as generating outputs from a high priority interrupt service routine (ISR), a sequencing circuit, or the like can be utilized without departing from the teachings of the present disclosure.

Figure 8:
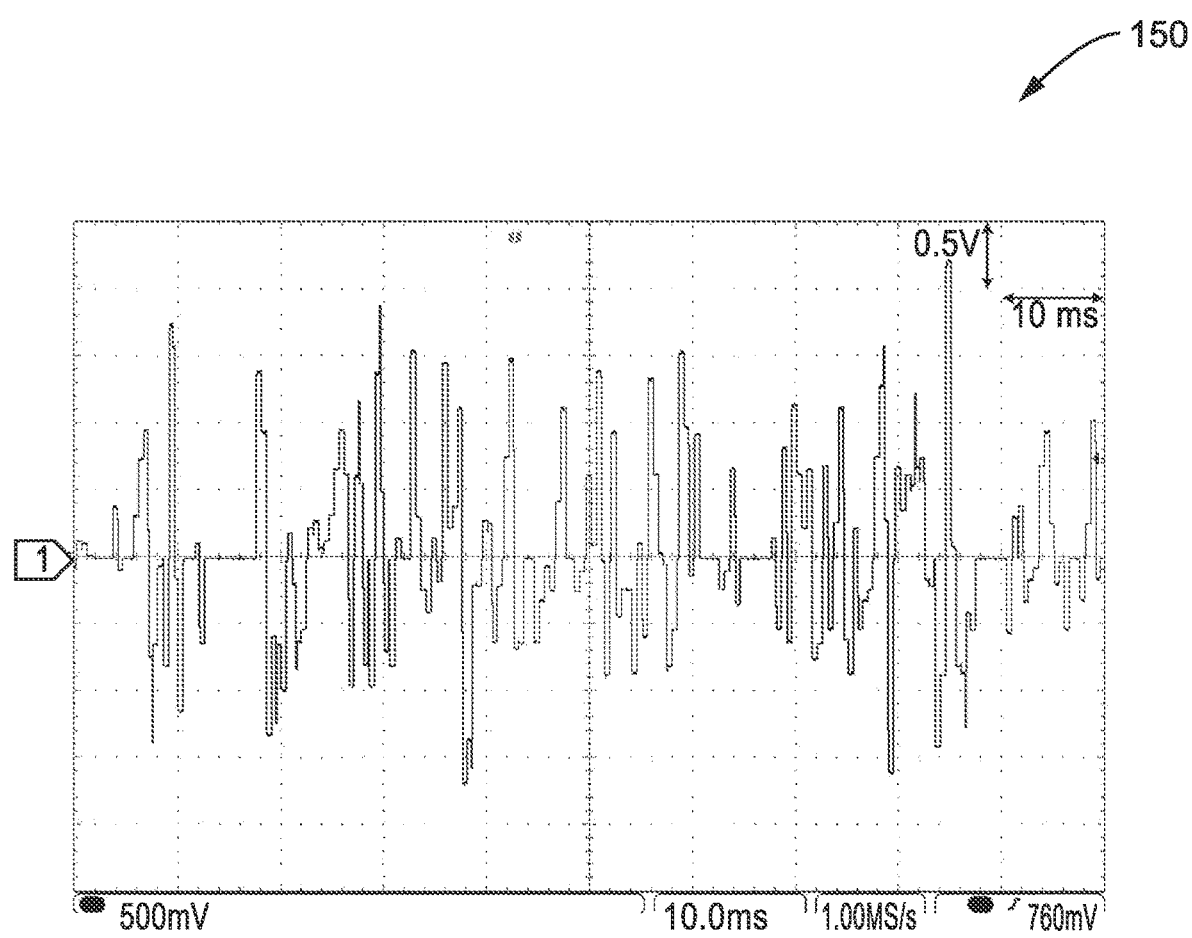
FIG. 8 is a waveform showing a continuous biomimetic current waveform achieved by combining multiple channels together into a single output, according to at least one embodiment of the present disclosure.

FIG. 8 illustrates an example waveform 150 produced by altering the circuit to eliminate the gap described above. The gap in this example was eliminated by altering the circuit to overcome the gap period by combining multiple stimulation channels with predetermined timing such that the gap in one channel is occupied by the current output of another, toward achieving a continuous biomimetic waveform without the gap seen in FIG. 7.

One potential issue of the biomimetic stimulation, e.g., EMG-mimetic pattern, is the charge imbalance induced by non-symmetric waveforms which can have some negative impact on neural tissues. This can be mitigated by the use of charge cancellation switching in the electrode array-stimulator circuit, which passively dissipates accumulated charges in the electrode/tissue interface. The timing of the discharge behavior can be controlled through a predetermined setting, which allows flexible user control to enable this function and tailor it for various stimulation protocols.

4. Conclusion

This present disclosure presents a novel biomimetic stimulator system integrated with an implantable neural interface stimulator circuit. The portable system can support concurrent multi-channel stimulation output with versatile stimulation parameters. Furthermore, the design can form the basis of a miniaturized wireless implantable system. At the time of this application, the prototype is being utilized for evaluating and improving biomimetic stimulation efficacy in retinal stimulation, spinal cord stimulation and others related applications, while further development is being done to increase closed-loop capabilities in this biomimetic stimulation system.

5. General Scope of Implementations

The enhancements described in the presented technology can be readily implemented within various biomimetic stimulation systems. It should also be appreciated that various portions of biomimetic stimulation systems are preferably implemented to include one or more computer processor devices (e.g., CPU, microprocessor, microcontroller, computer enabled ASIC, etc.) and associated memory storing instructions (e.g., RAM, DRAM, NVRAM, FLASH, computer readable media, etc.) whereby programming (instructions) stored in the memory are executed on the processor to perform the steps of the various process methods described herein.

Embodiments of the presented technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It should be appreciated that blocks at the beginning and end of these flowcharts, such as "Start" and "Stop" do not infer that the instructions are confined to a specific routine, or that it has an actual start and stop, per se, but are merely provided as points of reference in relation to executing steps involved in the process. The associated instructions for these process steps may be executed without limitation within various routines, tasks, slices, threads, and so forth, and these steps can be combined with steps to perform other functions, or can be extended to provide additional functionality, without departing from the teachings of the present disclosure.

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple implementations of the technology which include, but are not limited to, the following:

An apparatus for generating biomimetic stimulation from a neural implant, comprising: (a) a control unit configured for wirelessly receiving inputs from application programming for a user interface which executes on a mobile processor based electronics device; (b) a neural implant comprising a stimulator circuit coupled to an electrode array, wherein said stimulator circuit is configured for receiving inputs from said control unit and said neural implant is configured for being implanted proximal to target neural tissue; (c) wherein said control unit comprises a processor and non-transitory memory storing instructions executable by said processor, that when executed by the processor perform wirelessly collecting user inputs from application programming and generating biomimetic waveform outputs on desired stimulation channels with their amplitude and timing factors, and directing stimulation based on randomized inter-pulse-intervals (IPI) for multi-channel neural stimulation by steps comprising: (c)(i) generating stimulation command packets describing stimulation current to be generated in a biomimetic stimulation sequence; (c)(ii) precisely clocking these packets into a bit stream of stimulation data packets sent, through a wired or wireless interface, to the stimulator circuit; (d) wherein said stimulator circuit comprises circuitry comprising: (d)(i) a global most-significant-byte (MSB) controller and associated MSB stimulation current reference for setting the most significant byte of current control spanning all channels of said electrode array; (d)(ii) a local least-significant byte controller with associated output current source for each channel in said electrode array; (d)(iii) a processor and non-transitory memory storing instructions executable by said processor, that when executed by the processor perform steps comprising: (d)(iii)(A) receiving stimulation data packets from said control unit; (d)(iii)(B) converting an incoming stream of stimulation data packets from said control unit into actual stimulation signals for said global MSB controller and said local LSB controllers to the at least one electrode array; and (d)(iv) wherein current levels defined by the combination of said MSB and LSB controllers are utilized by said stimulator current sources to generate stimulation current to each electrode of said electrode array.

An apparatus for generating biomimetic stimulation from a neural implant, comprising: (a) a control unit; (b) a stimulator circuit configured for being implanted to provide concurrent multi-channel neural stimulation output through a plurality of stimulator channels; (c) wherein said control unit communicates with said stimulator circuit through a wired or wireless interface; (d) a user interface device configured for collecting user inputs for directing stimulation based on randomized inter-pulse-intervals (IPI) to direct multi-channel neural stimulation, comprising: (d)(i) receiving user input on average required randomized inter-pulse-intervals (IPI) and generating an array of IPI periods according to an exponential random distribution of pulse periods about a desired means of IPI following a uniform probability distribution in a given range and generating an array containing a set of stimulation parameters containing information on stimulation current pulses and randomized IPI values; (d)(ii) transmitting said stimulation parameters to said control unit; (e) wherein the combination of control unit and stimulator circuit are configured for performing direct control of amplitude and width of stimulation for each individual current pulse and their timing based on said stimulation parameters received from said user interface device for each of multiple stimulation output channels.

An apparatus for performing biomimetic stimulation for neural implants, comprising: (a) a control unit; (b) a stimulator circuit configured for being implanted to provide concurrent multi-channel neural stimulation output through a plurality of stimulator channels; (c) wherein said control unit communicates with said stimulator circuit through a wired or wireless interface; (d) user interface application programming configured for execution on a mobile device having a processor and non-transitory memory storing instructions executable by the processor, wherein said application programming is configured for performing steps comprising: (d)(i) wirelessly communicating user commands to said control unit; (d)(ii) storing prerecorded biomimetic stimulation waveform patterns; (d)(iii) allowing a user to select from performing stimulation based on waveform patterns or randomized inter-pulse-intervals (IPI) to direct multi-channel neural stimulation, comprising: (d)(iii)(A) retrieving a stored prerecorded biomimetic stimulation waveform pattern and generating a set of stimulation parameters for reproducing the desired signal waveform; and (d)(iii)(B) receiving user input on average required randomized inter-pulse-intervals (IPI) and generating an array of IPI according to an exponential random distribution of pulse periods about a desired means of IPI following a uniform probability distribution in a given range and generating an array containing a set of stimulation parameters containing information on stimulation current pulses and randomized IPI values; (d)(iv) wirelessly transmitting said stimulation parameters to said control unit for directing stimulation from said stimulator circuit; and (e) wherein the combination of control unit and stimulator circuit are configured for performing direct control of amplitude and width of each individual current pulse and their timing within the desired output waveform in response to receiving said stimulation parameters at said control unit and communicating commands to said stimulator circuit for outputting dynamic stimulation patterns comprising selected random pulse periods and/or biomimetic waveforms on multiple stimulation output channels.

An apparatus for generating biomimetic stimulation from a neural implant, comprising: (a) a control unit configured for wirelessly receiving inputs from a user interface device and its application programming configured for supplying user inputs to said control unit; (b) a neural implant comprising a stimulator circuit coupled to an electrode array, wherein said stimulator circuit is configured for receiving inputs from said control unit and said neural implant is configured for being implanted proximal to a target neural tissue; (c) wherein said control unit comprises a processor and non-transitory memory storing instructions executable by said processor, that when executed by the processor perform collecting user inputs from a user interface device on desired stimulation channels and their amplitude and timing factors, as well as biomimetic waveform outputs for directing stimulation based on randomized inter-pulse-intervals (IPI) to direct multi-channel neural stimulation in said stimulator circuit; (d) wherein said stimulator circuit comprises: (d)(i) circuitry for storing and controlling a global most-significant-byte (MSB) parameter and associated MSB stimulation current reference for setting the most significant byte of current control spanning all channels of said electrode array, and a local least-significant byte controller with associated output current source for each channel in said electrode array; (d)(ii) a processor and non-transitory memory storing instructions executable by said processor, that when executed by the processor perform steps comprising receiving and converting stimulation data packets from said control unit into actual stimulation signals for said global MSB controller and said local LSB controllers to said electrode array; and (iii) wherein current levels defined by the combination of said MSB and LSB controllers are utilized by said stimulator current sources to generate stimulation current to each electrode of said electrode array.

An apparatus for performing biomimetic stimulation for neural implants, comprising: (a) a control unit; (b) a stimulator circuit configured for being implanted to provide concurrent multi-channel neural stimulation output through a plurality of stimulator channels; (c) wherein said control unit communicates with said stimulator circuit through a wired or wireless interface; (d) wherein said control unit receives stimulation parameters from a user interface device, which are processed and communicated to said stimulator circuit as commands for each of the stimulator channels of said stimulator circuit; (e) wherein the combination of control unit and stimulator circuit are configured for performing direct control of amplitude and width of each individual current pulse and their timing within the desired output waveform driven by said stimulator circuit, and wherein dynamic stimulation patterns can be generated comprising random pulse periods and/or biomimetic waveform generation on multiple stimulation output channels; (f) wherein said stimulation on the output channels mimics biological signals.

A neural stimulator apparatus, comprising: (a) a control unit configured to wirelessly receive user settings for said neural stimulator apparatus from a user interface device; (b) a stimulator configured to communicate with the control unit; and (c) wherein said stimulator configured to perform concurrent multi-channel stimulation with independent arbitrary waveforms.

A neural interface system comprising a stimulator configured to provide stimulation waveforms mimicking standard biological signals.

A neural stimulator apparatus, comprising: (a) a 32-channel neural stimulator embedded in an implantable stimulator (b) said stimulator configured to perform concurrent multi-channel stimulation with independent arbitrary waveforms.

A neural stimulator apparatus, comprising: (a) a 32-channel neural stimulator embedded in an implantable stimulator (b) said stimulator configured to perform multi-channel stimulation mimicking electromyography (EMG) waveforms and randomly-spaced stimulation pulses mimicking neuronal firing patterns.

A neural stimulator apparatus, comprising: (a) a control unit configured to wirelessly communicate with a user interface device; and (b) a stimulator configured to communicate with the control unit; (c) wherein said stimulator configured to perform concurrent multi-channel stimulation with independent arbitrary waveforms.

A neural stimulator apparatus, comprising: (a) a control unit configured to wirelessly communicate with a user interface device; and (b) a stimulator configured to communicate with the control unit; (c) said stimulator configured to perform multi-channel stimulation mimicking electromyography (EMG) waveforms and randomly-spaced stimulation pulses mimicking neuronal firing patterns.

The apparatus or system of any preceding implementation, wherein said stimulator circuit comprises a system-on-chip (SoC) containing said global MSB controller and MSB stimulation current reference, multiple local LSB controllers and associated output current sources and comprising at least one processor and memory.

The apparatus or system of any preceding implementation, wherein said control unit is configured for communicating with said stimulator circuit using wired or wireless communications.

The apparatus or system of any preceding implementation, wherein said wireless communications from said control unit comprises a near-field Wireless Power Transfer (WPT) mechanism in which power is coupled to said stimulator circuit using an electromagnetic field, which is modulated for communicating data in either a single direction or bidirectionally between the control unit and stimulator circuit.

The apparatus or system of any preceding implementation, wherein said apparatus is configured for generating randomized period pulse trains.

The apparatus or system of any preceding implementation, wherein said randomized period pulse trains from said stimulator circuit are configured for use in retinal stimulation applications and EMG-mimetic stimulation patterns for spinal cord stimulation.

The apparatus or system of any preceding implementation, wherein said control unit is configured for collecting stimulation feedback from said stimulation circuit in establishing a closed-loop for directly updating or modifying stimulation parameters.

The apparatus or system of any preceding implementation, wherein said stimulator circuit further comprises: a feedback circuit coupled to the processor of said stimulator circuit; wherein said feedback circuit collects stimulation feedback which the processor of said stimulator circuit communicates back to the control unit to provide closed-loop capabilities in which feedback from said stimulator circuit is utilized for updating and/or modifying stimulation parameters.

The apparatus or system of any preceding implementation, wherein said control unit is configured for collecting said stimulation feedback from said stimulation circuit for directly updating or modifying stimulation parameters and/or packetizing the feedback for transmission to the user interface device.

The apparatus or system of any preceding implementation, wherein said apparatus is configured for performing simultaneous recording and stimulation, with a stimulation circuit that collects operational and/or neurological information.

The apparatus or system of any preceding implementation, wherein said stimulation parameters communicated to said control unit are derived from one or more pre-recorded biomimetic signals.

The apparatus or system of any preceding implementation, wherein said control unit receives stimulation parameters from a user interface device through wireless digital communications.

The apparatus or system of any preceding implementation, wherein said wireless digital communications comprises using a wireless fidelity (WiFi) standard for communications.

The apparatus or system of any preceding implementation, wherein said stimulator circuit comprises a system-on-chip (SoC).

The apparatus or system of any preceding implementation, wherein stimulation is performed with randomized inter-pulse-intervals (IPI), based on user input to the control unit from a user interface device on which the user enters an average required stimulation IPI, and programming on the user interface device generates an array of IPI according to an exponential random distribution of pulse periods about a desired means of IPI following a uniform probability distribution in a given range, with an array containing the parameters of the stimulation current pulses and the randomized IPI values are communicated to said control unit for directing stimulation from said stimulator circuit.

The apparatus or system of any preceding implementation, wherein said stimulator circuit comprises a system-on-chip (SoC).

The apparatus or system of any preceding implementation, wherein said apparatus is configured to provide closed-loop capabilities in supporting simultaneous recording and stimulation.

The apparatus or system of any preceding implementation, wherein the control unit is configured to send clock and commands to the stimulator for generating a stimulation output.

The apparatus or system of any preceding implementation, wherein the stimulator is configured to support wireless power and data transmissions via telemetry coils, wherein the stimulator is implantable, and wherein the control unit and stimulator are configured to communicate wirelessly.

As used herein, term "implementation" is intended to include, without limitation, embodiments, examples, or other forms of practicing the technology described herein.

As used herein, the singular terms "a," "an," and "the" may include plural referents unless the context clearly dictates otherwise. Reference to an object in the singular is not intended to mean "one and only one" unless explicitly so stated, but rather "one or more."

Phrasing constructs, such as "A, B and/or C", within the present disclosure describe where either A, B, or C can be present, or any combination of items A, B and C. Phrasing constructs indicating, such as "at least one of" followed by listing group of elements, indicates that at least one of these group elements is present, which includes any possible combination of these listed elements as applicable.

References in this specification referring to "an embodiment", "at least one embodiment" or similar embodiment wording indicates that a particular feature, structure, or characteristic described in connection with a described embodiment is included in at least one embodiment of the present disclosure. Thus, these various embodiment phrases are not necessarily all referring to the same embodiment, or to a specific embodiment which differs from all the other embodiments being described. The embodiment phrasing should be construed to mean that the particular features, structures, or characteristics of a given embodiment may be combined in any suitable manner in one or more embodiments of the disclosed apparatus, system or method.

In addition, when the disclosure refers to operations which "can" or "should" (or similar wording) be performed by the instructions, then this indicates that the operation is performed in at least one embodiment and/or mode of the present disclosure and more generally most of the embodiments and/or modes of the present disclosure, but that there could be instances, where for any of a variety of reasons, these instructions are overridden or otherwise not performed.

As used herein, the term "set" refers to a collection of one or more objects. Thus, for example, a set of objects can include a single object or multiple objects.

As used herein, the terms "approximately", "approximate", "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

It will be appreciated that the practice of some jurisdictions may require deletion of one or more portions of the disclosure after that application is filed. Accordingly the reader should consult the application as filed for the original content of the disclosure. Any deletion of content of the disclosure should not be construed as a disclaimer, forfeiture or dedication to the public of any subject matter of the application as originally filed.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for generating biomimetic stimulation from a neural implant, comprising:
   (a) a control unit;
   (b) a stimulator circuit configured for being implanted to provide concurrent multi-channel neural stimulation output through a plurality of stimulator channels;
   (c) wherein said control unit communicates with said stimulator circuit through a wired or wireless interface;
   (d) a user interface device configured for collecting user inputs for directing stimulation based on randomized inter-pulse-intervals (IPI) to direct multi-channel neural stimulation, comprising:
      (i) receiving user input on average required randomized inter-pulse-intervals (IPI) and generating an array of IPI according to an exponential random distribution of pulse periods about a desired average of IPI following a uniform probability distribution in a given range and generating an array containing a set of stimulation parameters containing information on stimulation current pulses and randomized IPI values;
      (ii) transmitting said stimulation parameters to said control unit;
   (e) wherein the combination of control unit and stimulator circuit are configured for performing direct control of amplitude and width of stimulation for each individual current pulse and their timing based on said stimulation parameters received from said user interface device for each of multiple stimulation output channels.

2. The apparatus of claim 1, wherein said stimulation parameters communicated to said control unit are derived from one or more pre-recorded biomimetic signals.

3. The apparatus of claim 2, wherein said control unit receives stimulation parameters from a user interface device through wireless digital communications.

4. The apparatus of claim 3, wherein said wireless digital communications comprises using a wireless fidelity (WiFi) standard for communications.

5. The apparatus of claim 1, wherein said stimulator circuit comprises a system-on-chip (SoC).

6. The apparatus of claim 1, wherein said control unit is configured for communicating with said stimulator circuit using wired or wireless communications.

7. The apparatus of claim 6, wherein said wireless communications from said control unit comprises a near-field Wireless Power Transfer (WPT) mechanism in which power is coupled to said stimulator circuit using an electromagnetic field, which is modulated for communicating data in either a single direction or bidirectionally between the control unit and stimulator circuit.

8. The apparatus of claim 1, wherein said apparatus is configured for generating randomized period pulse trains for a stimulator circuit for use in retinal stimulation applications and EMG-mimetic stimulation patterns for spinal cord stimulation.

9. The apparatus of claim 1, wherein said control unit is configured for collecting stimulation feedback from said stimulation circuit in establishing a closed-loop for directly updating or modifying stimulation parameters.

10. The apparatus of claim 9, wherein said apparatus is configured for recording said stimulation feedback.

11. The apparatus of claim 10, wherein said stimulation feedback is recorded at said control unit or transmitted from said control to a remote device.

12. An apparatus for performing biomimetic stimulation for neural implants, comprising:
a control unit;
a stimulator circuit configured for being implanted to provide concurrent multi-channel neural stimulation output through a plurality of stimulator channels;
wherein said control unit communicates with said stimulator circuit through a wired or wireless interface;
wherein said control unit receives stimulation parameters from a user interface device, which are processed and communicated to said stimulator circuit as commands for each of the stimulator channels of said stimulator circuit;
wherein the combination of control unit and stimulator circuit are configured for performing direct control of amplitude and width of each individual current pulse and their timing within the desired output waveform driven by said stimulator circuit, and wherein dynamic stimulation patterns can be generated comprising random pulse periods and/or biomimetic waveform generation on multiple stimulation output channels;
wherein said stimulation on the output channels mimics biological signals; and
wherein stimulation is performed with randomized inter-pulse-intervals (IPI), based on user input to the control unit from a user interface device on which the user enters an average required stimulation IPI, and programming on the user interface device generates an array of IPI according to an exponential random distribution of pulse periods about a desired average of IPI following a uniform probability distribution in a given range, with an array containing the parameters of the stimulation current pulses and the randomized IPI values are communicated to said control unit for directing stimulation from said stimulator circuit.

13. The apparatus of claim 12, wherein said stimulation parameters communicated to said control unit are derived from one or more pre-recorded biomimetic signals.

14. The apparatus of claim 13, wherein said control unit receives stimulation parameters from a user interface device through wireless digital communications.

15. The apparatus of claim 14, wherein said wireless digital communications comprises using a wireless fidelity (WiFi) standard for communications.

16. The apparatus of claim 12, wherein said stimulator circuit comprises a system-on-chip (SoC).

17. The apparatus of claim 12, wherein said stimulator circuit is configured for communicating with said control unit using wired or wireless communications.

18. The apparatus of claim 12, wherein said wireless communications is supplied by a near-field Wireless Power Transfer (WPT) mechanism in which power is coupled to said stimulator circuit using an electromagnetic field, which is modulated for communicating data in either a single direction or bidirectionally between the control unit and stimulator circuit.

19. The apparatus of claim 12, wherein said stimulator circuit further comprises:
a feedback circuit which collects stimulation feedback which said stimulator circuit communicates back to said control unit to provide closed-loop capabilities in which feedback from said stimulator circuit is utilized for updating and/or modifying stimulation parameters.

20. The apparatus of claim 19, wherein said control unit is configured for collecting said stimulation feedback from said stimulation circuit for directly updating or modifying stimulation parameters and/or packetizing the feedback for transmission to the user interface device.

21. The apparatus of claim 19, wherein said apparatus is configured to provide closed-loop capabilities in supporting simultaneous recording and stimulation.

22. An apparatus for performing biomimetic stimulation for neural implants, comprising:
(a) a control unit;
(b) a stimulator circuit configured for being implanted to provide concurrent multi-channel neural stimulation output through a plurality of stimulator channels;
(c) wherein said control unit communicates with said stimulator circuit through a wired or wireless interface;
(d) user interface application programming configured for execution on a mobile device having a processor and non-transitory memory storing instructions executable by the processor, wherein said application programming is configured for performing steps comprising:
(i) wirelessly communicating user commands to said control unit;
(ii) storing prerecorded biomimetic stimulation waveform patterns;
(iii) allowing a user to select from performing stimulation based on waveform patterns or randomized inter-pulse-intervals (IPI) to direct multi-channel neural stimulation, comprising:
(A) retrieving a stored prerecorded biomimetic stimulation waveform pattern and generating a set of stimulation parameters for reproducing the desired signal waveform; and
(B) receiving user input on average required randomized inter-pulse-intervals (IPI) and generating an array of IPI according to an exponential random distribution of pulse periods about a desired average of IPI following a uniform probability distribution in a given range and generating an array containing a set of stimulation parameters containing information on stimulation current pulses and randomized IPI values;
(iv) wirelessly transmitting said stimulation parameters to said control unit for directing stimulation from said stimulator circuit; and
(e) wherein the combination of control unit and stimulator circuit are configured for performing direct control of amplitude and width of each individual current pulse and their timing within the desired output waveform in response to receiving said stimulation parameters at said control unit and communicating commands to said stimulator circuit for outputting dynamic stimulation patterns comprising selected random pulse periods and/or biomimetic waveforms on multiple stimulation output channels.

* * * * *